United States Patent [19]

Sayka et al.

[11] Patent Number: 5,313,818
[45] Date of Patent: May 24, 1994

[54] CONTAMINANT MONITOR FOR A FLOWING LIQUID

[75] Inventors: Anthony Sayka; Christopher D. Reynes, both of San Antonio; Bradley G. Williams, Castroville; Gerardo F. Martinez, San Antonio, all of Tex.

[73] Assignee: VLSI Technology, Inc., San Jose, Calif.

[21] Appl. No.: 976,060

[22] Filed: Nov. 12, 1992

[51] Int. Cl.⁵ ............................................. G01N 7/14
[52] U.S. Cl. .................................................... 73/19.1
[58] Field of Search ................. 73/19.01, 19.04, 19.05, 73/19.06, 19.10, 19.11

[56] References Cited

U.S. PATENT DOCUMENTS

| | | | |
|---|---|---|---|
| 3,060,723 | 10/1962 | Kapff et al. | 73/19.04 |
| 3,225,585 | 12/1965 | Wohnoutka | 73/19.10 |
| 3,381,518 | 5/1968 | Loehle | 73/19.11 |
| 3,844,160 | 10/1974 | Yamaoka | 73/19.11 |
| 5,134,962 | 8/1992 | Amada et al. | 73/40 X |

FOREIGN PATENT DOCUMENTS

264295 1/1989 German Democratic Rep. ................. 73/19.11

838532 6/1981 U.S.S.R. ............................ 73/19.10

*Primary Examiner*—Hezron E. Williams
*Assistant Examiner*—Joseph W. Roskos
*Attorney, Agent, or Firm*—Hickman & Beyer

[57] ABSTRACT

A method for detecting bubbles in a liquid characterized by the steps of: a) flowing a liquid through a chamber; b) allowing bubbles in the liquid to escape within the chamber; and c) sensing the gaseous volume within the chamber to determine whether any gas bubbles were present in the liquid. An apparatus of the present invention includes a sealed chamber, a pump for pumping a liquid through the sealed chamber, and a mechanism for detecting gaseous accumulation within the chamber. The mechanism for detecting gaseous accumulation preferably includes a floating device having a float portion and a magnet portion, and a magnetic detector for detecting the magnetic field strength generated by the magnet portion. The magnetic field strength can be used to calculate the liquid level within the chamber which can, in turn, used to calculate the gaseous volume within the chamber. An analyzer coupled to the magnetic detector may produce a detection signal when the gaseous volume exceeds a predetermined criteria to alarm an operator that excessive amount of bubbles are present in the liquid.

17 Claims, 3 Drawing Sheets

5,313,818

CONTAMINANT MONITOR FOR A FLOWING LIQUID

BACKGROUND OF THE INVENTION

1. Field of the Invention

This invention relates to a system for discovering defects in liquids, and more particularly to a system for detecting bubbles in a liquid being applied to a surface of a semiconductor wafer.

2. Background of the Technical Art

Liquids are used in a broad range of manufacturing processes. In one class of processes, a liquid is applied to a workpiece as a coating to form a temporary or permanent layer used in making the product. Such products include optical lenses and filters, magnetic disk surfaces for computers, compact disk surfaces, abrasives and adhesive films for surfaces. Of particular interest in this discussion are liquids used to manufacture semiconductor wafers for the electronics industry, where the ultimate products are integrated circuits (ICs) formed from these wafers. Unless the liquids used in fabricating semiconductor wafers satisfy stringent chemical, physical and electrical specifications, production yields of working IC's will be less than desired.

A common fabrication technique is the spin-on coating (SOC) of selected liquids. In a SOC process, a liquid, such as photoresist or a dielectric, is applied to a spinning wafer to produce a thin coating on the wafer. One type of spin-on coating process, called spin-on glass (SOG) coating process, forms a dielectric glass layer, such as a layer of silicon dioxide, on a wafer surface. In another type of SOC process, photoresist material is applied as a coating to an exposed surface.

Problems in SOC processes arise if the liquid supplied to a workpiece contains gas bubbles. Bubbles can reduce the dose of liquid applied to a wafer surface, and can cause irregularities in the resultant film.

Using present technology, the presence of gas bubbles (referred to simply as "bubbles" here) in a deposited liquid is not detected until after processed wafers are completed and when low yields become apparent. This is because present-day delivery systems are sealed to prevent contamination. For example, an SOC liquid is typically delivered to a production facility in a sealed bottle. This bottle is tapped for pumping the liquid by a liquid-handling system. The liquid-handling system is also sealed to minimize exposure of the process liquid to contaminants.

Bubbles can be present in the liquid when delivered, and can also be introduced into the liquid during transport from the bottle to the application point. Also, in present SOC systems, a small air gap separates the end of the liquid pipeline from the workpiece. The liquid is therefore exposed to contaminants present in air when crossing that gap, and may pick up particles or gas bubbles.

What is needed is a system for detecting and preferably removing bubbles in a liquid reagent, thereby improving process yields during the production of integrated circuits.

SUMMARY OF THE INVENTION

These needs are met by the invention, which provides a method for detecting the presence of bubbles in a flowing liquid reagent, for providing a quantitative measure of the volume of any such bubbles, and for trapping at least some of the bubbles before the liquid is applied to a workpiece.

In one embodiment of the invention, a liquid is caused to flow through a chamber. Bubbles in the liquid tend to float upwardly to occupy an upper volume of the chamber. In the absence of bubbles, the top surface of the chamber lies at a known height h2 above the top surface of the liquid. The ceiling of the chamber is at a height h1 above the top surface of the liquid in the chamber when bubbles are present. The height or separation difference h1−h2 is detected to determine whether the liquid presently contains any bubbles therein. The heights h1 and h2 may be determined by apparatus, such as a magnetic field source and a magnetic field detector, that quantitatively senses the separation distance between the ceiling of the chamber and the top surface of the liquid in the chamber.

Apparatus for detecting the presence of bubbles in a flowing liquid includes a housing defining a chamber that receives a flowing liquid and allows for separation of bubbles contained in the liquid. The chamber has a lower chamber portion through which the liquid flows. The chamber also has an upper chamber portion in which gasses caused by bubbles can accumulate. The apparatus also includes distance sensing means for sensing the height of the liquid in the chamber to determine whether the liquid included any bubbles. Contaminant particles, if any are present, sink to the bottom or remain suspended in the liquid and produce no liquid level change.

Additional features and advantages of the invention are described specifically by the preferred embodiments set forth below.

DETAILED DESCRIPTION OF THE PREFERRED EMBODIMENTS

Reference will now be made in detail to the preferred embodiments of the invention, examples of which are illustrated in the accompanying drawings. Although the invention will be described in conjunction with the preferred embodiments, it should be understood that these illustrations are not intended to limit the invention to those embodiments. The invention is intended to cover alternatives, modifications and equivalents, which may be included within the spirit and scope of the invention, as defined by the appended claims.

Figure 1:
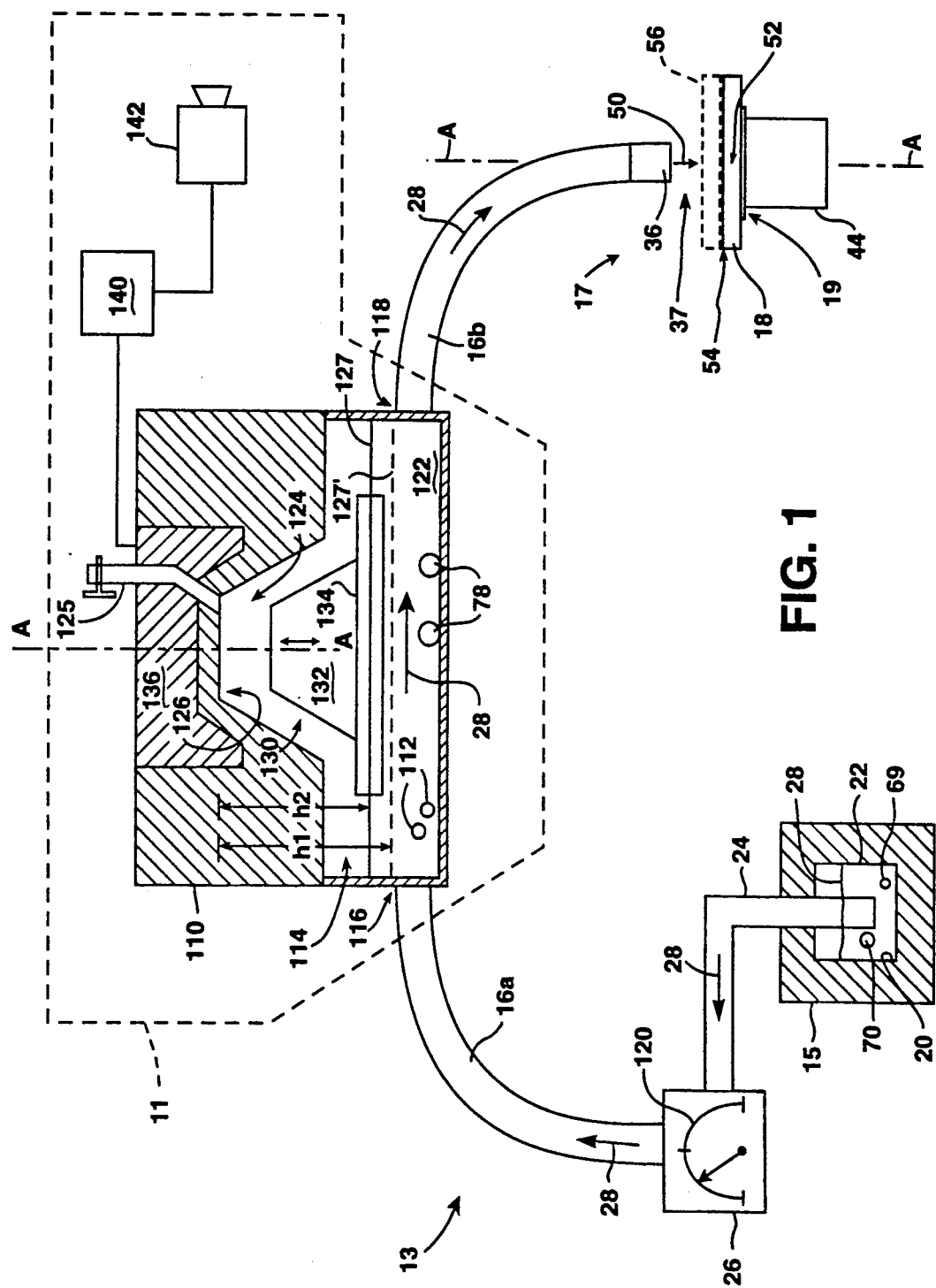
FIG. 1 is a pictorial view of a first embodiment of the invention.

FIG. 1 illustrates an embodiment of a monitoring system 11 for use in a spin-on coating (SOC) system 13. SOC system 13 includes a source 15 of SOC liquid. An SOC liquid may include a photoresist material in a solvent or a liquid dielectric material, delivered through conduits 16a and 16b to an SOC process site 17 remote from the source 15. At the process site 17, a workpiece 18 is secured to a turntable 19 which can rotate around a vertical axis A.

The workpiece 18 is typically a semiconductor wafer. The diameter of the workpiece 18 is preferably larger than the diameter of the turntable 19, to minimize contamination of the turntable with excess coating liquid. For example, a workpiece or wafer 18 having a six-inch diameter is supported on the turntable 19 (e.g., by a vacuum chuck forming part of the turntable) having a three-inch diameter. With this arrangement, virtually all the excess SOC liquid is spun off the workpiece 18 without contaminating the turntable 19.

While the workpiece 18 rotates, a volume of SOC liquid is released from the conduit 16b onto the center of the workpiece. In alternative constructions, the conduit 16b mounts on a translating arm (not shown) and sweeps across the workpiece 18, dispensing liquid as it sweeps. In either case, centrifugal forces generated by the rotating workpiece 18 disperse the liquid over the surface of the workpiece to form a desired coating layer.

The SOC liquid source 15 has a chamber 20 receptive to a bottle 22 of SOC liquid. The bottle 22 is tapped by a feed pipe 24. The feed pipe 24 is coupled to a regulated pump mechanism 26, which regulates the flow of SOC liquid. Preferably, the liquid 28 contains no bubbles of gas or contaminant particles, such as a bubble 69 or a particle 70.

Conduit 16a is connected between the pump mechanism 26 and the monitoring system 11. Conduit 16b is connected between the monitoring system 11 and a nozzle 36. The nozzle 36 is located close to and is directed toward the center of the workpiece 18. At the liquid application site 17, a gap 37 separates the nozzle 36 from the workpiece 18. The gap 37 is provided to avoid physical contact between nozzle 36 and workpiece 18 and to allow liquid 28 to disperse properly onto the workpiece 18. The workpiece 18 is typically a substrate or semiconductor wafer. The SOC liquid 28 is often a polymeric photoresist material in a solvent, such as Shipley AZ-1370 or Hunt Waycoat SC 100, or a liquid dielectric substance, such as spin-on glass or polyimide.

During operation of the SOC system 13, the platform 19, which preferably includes a vacuum chuck (not shown) to securely hold the workpiece 18, is rotated at an angular velocity of between 100 and 5500 revolutions per minute by a motor 44. The angular velocity chosen for the platform 19 depends on the particular SOC liquid 28 being used and on the particular step in the overall SOC procedure being performed, as is well known to those skilled in the art.

The SOC liquid 28 is dispersed over the top surface of the rotating workpiece 18 to form a new layer 56 on an exposed surface of the workpiece 18. Because the workpiece 18 is rotating, centrifugal force disperses the liquid 28 outward from the workpiece center 52 toward the circumference 54 of the workpiece 18.

Defects in the SOC liquid 28 can produce flaws in a wafer 18 that degrade the operational characteristics of that wafer. Some wafers are extensively flawed and must be scrapped; other wafers that suffer less damage must be reworked. Scrapping or reworking adds to integrated circuit production costs.

The monitoring system 11 is used to provide early detection and removal of bubbles in the SOC liquid and to trap contaminant particles. The monitoring system 11 includes an enclosure 110 defining a chamber 114 for separating bubbles 112 and particles 78 from the liquid 28. The liquid 28 is pumped through the conduit 16a into the chamber 114 through a chamber inlet 116. The liquid 28 flows out of the chamber 114 through a chamber outlet 118 and conduit 16b. The pump mechanism 26 includes or is coupled to a regulator 120 that controls the rate at which liquid 28 is pumped through the chamber 114.

The chamber 114 includes a liquid reservoir 122 that occupies a lower part of the chamber and a gas reservoir 124 that occupies an upper part of the chamber. A gas bleed valve assembly 125 is provided to selectively release gas from the gas reservoir 124, such as when the gas reservoir volume becomes too large. As liquid 28 flows through the chamber 114, solid contaminant particles 78 tend to settle to the bottom of the chamber 114. Gas bubbles 112 contained in the liquid 28 tend to float to the surface of the liquid and then join the gas reservoir 124. If a bubble 112 leaves the liquid 28 within the chamber 114, the level of liquid within the liquid reservoir 122 will be forced downwardly. Therefore, the release of bubbles from the liquid 28 within chamber 114 produces a change in the liquid level of reservoir 122 from an initial depth to a lower depth. This change in depth is detected by a sensor, discussed below.

It should be noted that not all of the bubbles 112 will escape from the liquid 28 before exiting the chamber 114. Therefore, the volume of gas in the gas reservoir 124 is merely a representation of the total bubble volume within the liquid passing through the chamber 114.

The monitoring system 11 further includes a floating device 130 having a float portion 134 and a truncated, conical magnet portion 132. The magnet portion 132 rests near to or against a chamber ceiling 126 when the liquid 28 flowing through the chamber is substantially bubble-free. The chamber ceiling 126 preferably has a complementary shape to the magnet portion 132. If bubbles 112 are present in the liquid 28, the gas from the bubbles tends to collect in the gas reservoir 124. The increased volume in gas reservoir 124 forces the level of the liquid reservoir 122 to drop.

The magnetic portion 132 is preferably a permanent magnet. The float portion 134 is preferably made from a low density, non-contaminating material such as polypropylene.

The chamber ceiling 126 includes or has attached thereto a magnetic field detector 136. As the depth of reservoir 122 changes, the magnetic field sensed by the field detector 136 changes correspondingly. Magnetic field detectors (such as reed switches, etc.) are commercially available.

With no bubbles present in the liquid 28, the separation h between the magnetic portion 132 and the field detector 136 is a selected distance $h = h2$, and the liquid surface level is shown at 127. If bubbles are present, the distance increases to a value $h = h1 > h2$ that characterizes the cumulative volume of bubbles that have separated from the liquid 28 within the chamber 114, and the level of the liquid is shown at 127'. Again, not all of the bubbles in the liquid 28 flowing through the chamber 114 will necessarily escape from the liquid and join with the gaseous volume within the chamber.

The field detector 136 may be connected to a microprocessor or other computing means 140 that calculates the change in liquid depth of liquid reservoir 122 as a function of the magnetic field strength sensed at the field detector 136. If the change of depth exceeds a selected threshold, the computing means 140 may signal the user, such as by activation of an alarm 142, that the liquid 28 contains entrained bubbles, some of which may be reaching the workpiece or wafer 18. In response to such alarm, the user has at least two options. The user can check the bottle 22 of liquid to determine if this source of liquid contains an unacceptably large number of bubbles. The user can also check the system connections to eliminate air leaks, and/or purge from the system the liquid carrying the bubbles.

Figure 2:
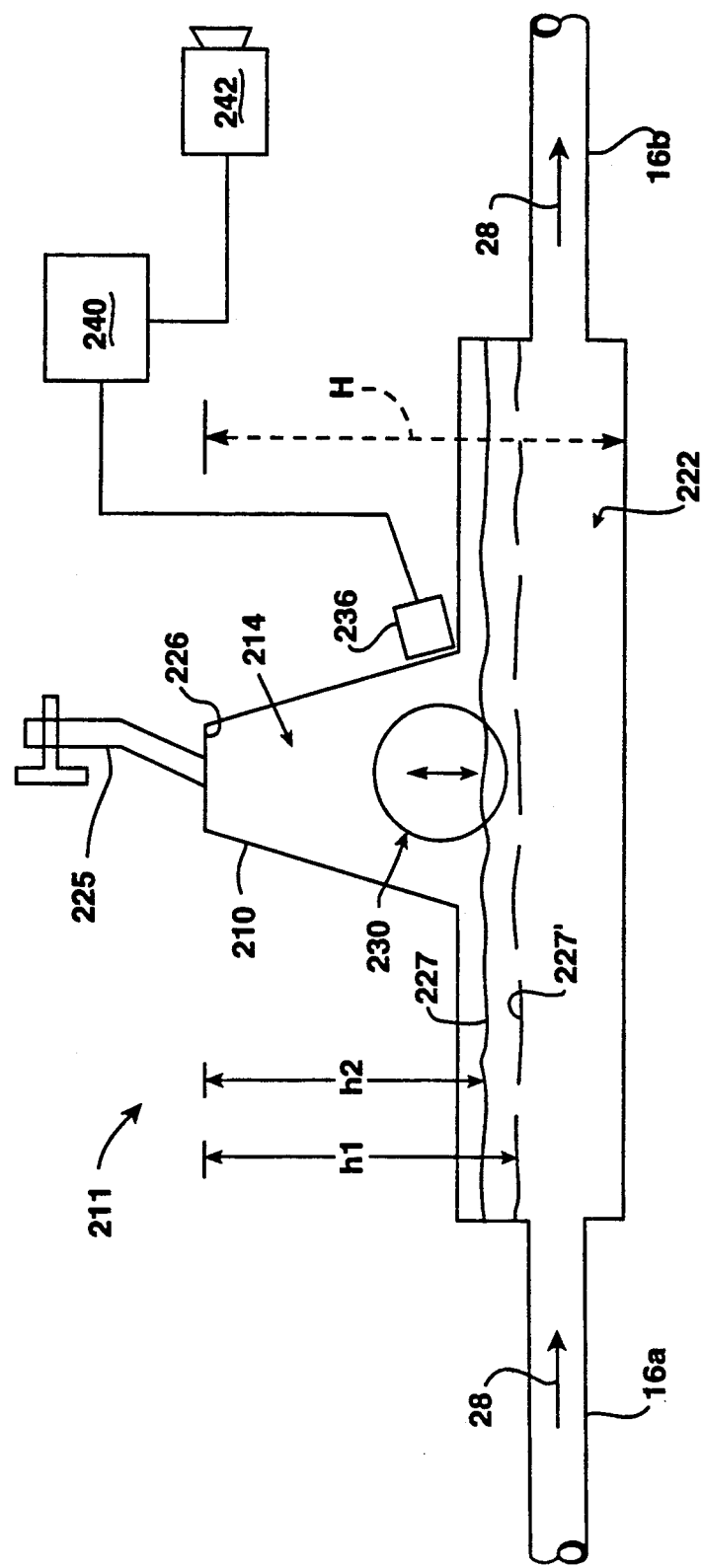
FIG. 2 is a pictorial view of a second embodiment of the invention.

FIG. 2 illustrates a second embodiment 211 of a liquid monitoring system. The monitoring system 211 of FIG. 2 differs from the monitoring system 11 of FIG. 1 primarily in the structure of the floating device 230. In the embodiment of FIG. 2, floating device 230 includes a floating sphere, an oblate or prolate spheroid, or cylinder provided with or enclosing a magnetic material. Floating device 230 can, for example, comprise a hollow plastic ball having a magnet glued inside. A magnetic field detector 236 is positioned on the outside of a chamber wall 210. The total chamber height H, measured from the bottom of liquid reservoir 222 to the interior of the ceiling 226 of the chamber 214, can be changed during manufacture of the system 211 to suit the particular needs of the user. A vent assembly 225 may be provided to release gas from the chamber. A computation device 240 coupled to an alarm 242 can be used to warn a user of the presence of entrained bubbles in the liquid being applied to a workpiece, such as when the liquid level drops from the level shown at 227 to the level shown at 227'.

The monitoring systems illustrated in FIGS. 1 and 2 are preferably sealed to minimize exposure of the liquid to air or other contaminants. The conduit 16a in FIGS. 1 and 2 is preferably completely filled with liquid.

Figure 4:
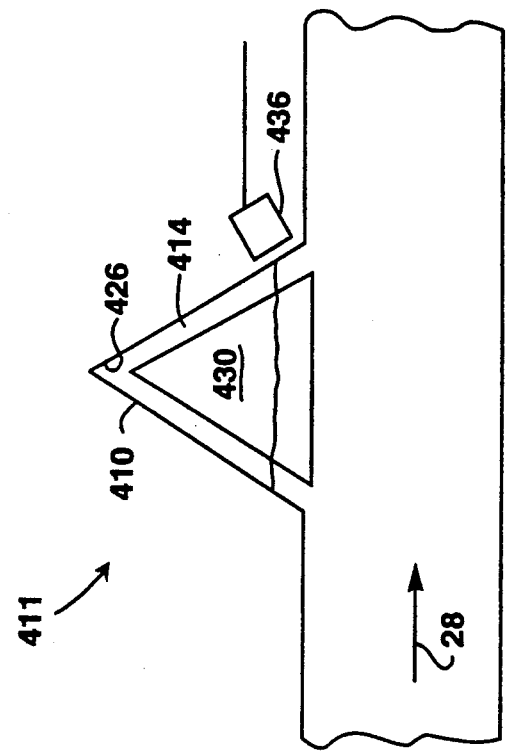
FIG. 4 is a partial pictorial view of a fourth embodiment of the invention.
Figure 3:
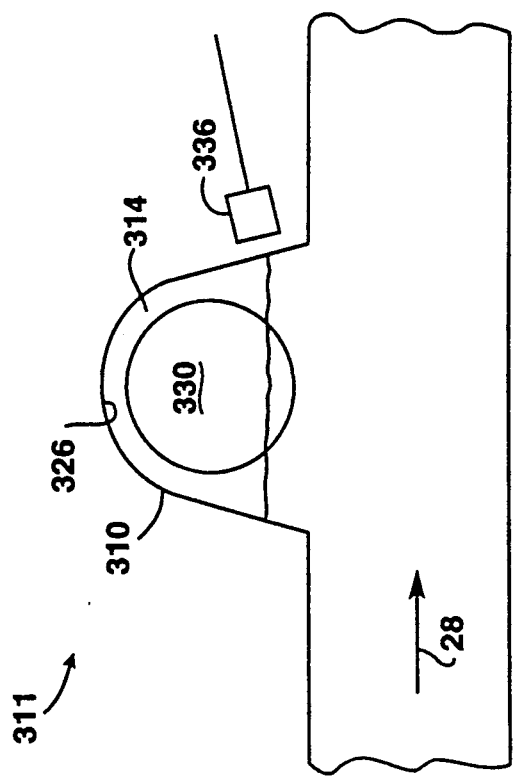
FIG. 3 is a partial pictorial view of a third embodiment of the invention.

FIGS. 3 and 4 show a third embodiment 311 and a fourth embodiment 411, respectively, of the liquid monitoring system. In the embodiment 311 of FIG. 3, a floating device 330, having a spherical or cylindrical shape, is provided in a chamber 314 that communicates with the SOC liquid 28. A housing 310 having a ceiling 326, having a complementary shape to the floating device 330, defines the chamber 314. A magnetic field detector 336 is positioned adjacent to the housing 310. The floating device 330 preferably includes a magnetic source as described previously. The positions of the field source 332 and the field detector 336 may be exchanged with each other.

In the embodiment 411 of FIG. 4, a floating device 430, having the shape of a pyramid or triangular prism, is provided in a chamber 414 that receives the SOC liquid 28. The floating device 410 includes a magnetic material as described previously. A housing 410 having a ceiling 426, having a complementary shape to the floating device 430, defines the chamber 414. A magnetic field detector 436 is positioned adjacent to housing 410.

The monitoring system 311 in FIG. 3 and 411 in FIG. 4 provide increased sensitivity to the release of bubbles from SOC liquid 28 because the volumes of the chambers 314 and 414, respectively, are only slightly greater than the volumes of the floating devices 332 and 432, respectively. In consequence, even a small number of bubbles will cause a discernible movement of the floating devices.

The foregoing preferred embodiments illustrate several detailed examples of the system for practicing the claimed invention. However, variation and modification may be made in these embodiments without departing from the scope of the invention.

What is claimed is:

1. A method for detecting bubbles in a liquid prior to applying said liquid to a surface of a workpiece comprising the steps of:

flowing a liquid through a low restrictive chamber that has a chamber ceiling, wherein said liquid is a viscous liquid used as a spin-on-coating for a workpiece;

allowing bubbles in said liquid to escape from said liquid and to join a gaseous volume within said chamber located between a surface of said liquid and said chamber ceiling;

sensing said gaseous volume within said chamber to determine whether said liquid contains bubbles; and applying said liquid to a surface of a workpiece.

2. A method for detecting bubbles as recited in claim 1 wherein said step of flowing a liquid through a chamber comprises pumping a liquid through a sealed chamber.

3. A method for detecting bubbles as recited in claim 1 further comprising the step of trapping at least some of said bubbles and at least some particles carried by said liquid within said chamber.

4. A method for detecting bubbles in a liquid comprising the steps of:

flowing a liquid through a chamber that has a chamber ceiling;

allowing bubbles in said liquid to escape from said liquid and to join a gaseous volume within said chamber located between a surface of said liquid and said chamber ceiling;

providing a floating device within said chamber to float on said surface of said liquid; and sensing the height of said floating device within said chamber to determine whether said liquid contains bubbles.

5. A method for detecting bubbles as recited in claim 4 wherein said floating device includes a float portion and a magnet portion, and wherein said step of sensing the height of said floating device comprises sensing the magnetic field strength of said magnet portion.

6. A method for detecting bubbles as recited in claim 5 wherein said magnet portion is configured as the complement of said chamber ceiling.

7. A method for detecting bubbles as recited in claim 5 further comprising the step of comparing said magnetic field strength of said magnet portion against a predetermined criteria, and developing a detection signal when said magnetic field strength is related to said predetermined criteria in a predetermined fashion.

8. A bubble detector for a spin-on coating apparatus comprising:

a low restrictive chamber having a chamber ceiling;

means for continuously pumping a viscous liquid used for spin-on coating through said chamber for application to the surface of a workpiece;

means for detecting a volume of gas within said chamber located between said chamber ceiling and a surface of said liquid; and means for applying said liquid to a surface of a workpiece.

9. A bubble detector as recited in claim 8 wherein said chamber is a sealed chamber.

10. A bubble detector as recited in claim 9 wherein said means for pumping said liquid comprises a metering pump.

11. A bubble detector comprising:

a chamber;

means for pumping a liquid through said chamber;

means for detecting gaseous accumulation within said chamber including a floating device disposed within said chamber.

12. A bubble detector as recited in claim 11 wherein said floating device comprises a float portion and a magnet portion.

13. A bubble detector as recited in claim 12 wherein said magnet portion is configured to complement a ceiling surface of said chamber.

14. A bubble detector as recited in claim 11 further comprising a magnetic detector for detecting the magnetic field strength of said magnet portion.

15. A bubble detector as recited in claim 14 further comprising analyzer means coupled to said magnetic detector for comparing said magnetic field strength against a predetermined criteria.

16. A bubble detector as recited in claim 15 wherein said analyzer means is operative to develop a detection signal when said magnetic field strength is related to said predetermined criteria in a predetermined fashion.

17. A bubble detector as recited in claim 16 further comprising alarm means responsive to said detection signal.

* * * * *